United States Patent
Crowley et al.

(10) Patent No.: US 9,119,790 B2
(45) Date of Patent: Sep. 1, 2015

(54) PHARMACEUTICAL COMPOSITION

(75) Inventors: Michael Crowley, Norwich, NY (US);
Amanda Gage, Norwich, NY (US);
Jack Maegli, Beloit, WI (US); Timothy O'Reilly, Norwich, NY (US)

(73) Assignee: ZENBURY INTERNATIONAL LIMITED, Tralee (IE)

( * ) Notice: Subject to any disclaimer, the term of this patent is extended or adjusted under 35 U.S.C. 154(b) by 70 days.

(21) Appl. No.: 13/498,528

(22) PCT Filed: Sep. 24, 2010

(86) PCT No.: PCT/EP2010/064182
§ 371 (c)(1),
(2), (4) Date: Mar. 27, 2012

(87) PCT Pub. No.: WO2011/036270
PCT Pub. Date: Mar. 31, 2011

(65) Prior Publication Data
US 2012/0184627 A1  Jul. 19, 2012

(30) Foreign Application Priority Data
Sep. 28, 2009  (IE) .................................. S2009/0746

(51) Int. Cl.
*A61K 47/26* (2006.01)
*A61K 47/36* (2006.01)
*A61K 47/04* (2006.01)
*A61K 47/38* (2006.01)
*A61K 9/20* (2006.01)
*A61K 9/16* (2006.01)

(52) U.S. Cl.
CPC ............. *A61K 9/2013* (2013.01); *A61K 9/2009* (2013.01); *A61K 9/2018* (2013.01); *A61K 9/2054* (2013.01); *A61K 9/2095* (2013.01); *A61K 9/1611* (2013.01); *A61K 9/1617* (2013.01); *A61K 9/1623* (2013.01); *A61K 9/1652* (2013.01)

(58) Field of Classification Search
CPC ............ A61K 2300/00; A61K 9/2054; A61K 47/48969; A61K 47/4823; A61K 47/48338; A61K 47/48215; A61K 31/337; A61K 31/7048; A61K 47/48176; A61K 47/48192; A61K 47/482; A61K 9/2018; A61K 9/2077
See application file for complete search history.

(56) References Cited

U.S. PATENT DOCUMENTS 7,060,294 B2 *  6/2006  Batra et al. .................... 424/464
2005/0220865 A1 * 10/2005  Koleng et al. ................. 424/451
2007/0190147 A1  8/2007  Solomon et al.

OTHER PUBLICATIONS

"Tablet: Formulation of tablets/Diluents" from Pharmpedia: The Free Pharmaceutical Encyclopedia; XP002608668; [Online]; Aug. 8, 2005, pp. 1-6. See entry "2" on p. 2 of 2 of IDS filed Apr. 17, 2012 for U.S. Appl. No. 13/498,528.*
"Tablet: Formulation of tablets/Diluents" from Pharmpedia: The Free Pharmaceutical Encyclopedia; XP002608668; [Online]; Aug. 8, 2005, Included in IDS filed Apr. 17, 2012.*
"Sucrose" entry at ChemSpider online. http://www.chemspider.com/Chemical-Structure.5678.html; Sep. 9, 2013.*
Anonymous: "Tablet: Formulation of tablets/Diluents" From Pharmpedia: The Free Pharmaceutical Encyclopedia; XP002608668; [Online]; Aug. 8, 2005, p. 6pp.
Gohel, M.C. et al: "A review of co-processed directly compressible excipients."; J Pharm Pharmaceut Sci, vol. 8, No. 1, Apr. 16, 2005, pp. 76-93, XP002608670; the whole document.
Jones, D.S. et al/ Paper 1: "Formulation and characterisation of hot melt extruded dosage forms: challenges and opportunities" In: "Pharmaceutical Polymers" 2007, Rapra Technology Limited, XP002608675 p. 2.
Rowe, R.C. et al: "Handbook of Pharmaceutical Excipients, 5th edition" 2006, Pharmaceutical Press, XP002608669; pp. 430, 744.
Satish K. Nachaegari and Arvind K. Bansal: "Coprocessed Excipients for Solid Dosage Forms"; Pharmaceutical Technology, Jan. 2004, pp. 52-64; XP002608671; the whole document.
European Intention to grant issued in European Patent Application No. 10 759 624.9 on Apr. 9, 2014.

* cited by examiner

*Primary Examiner* — Audrea Buckley
(74) *Attorney, Agent, or Firm* — Birch, Stewart, Kolasch & Birch, LLP

(57) ABSTRACT

The invention concerns a co-processed additive for a solid-dose pharmaceutical composition, the additive comprising from about 50% to 99.5% by weight of at least one pharmaceutical compression aid and from about 0.5% to 50% by weight of at least one pharmaceutical lubricant, the melting point of said compression aid(s) being higher than the melting point of said lubricant(s). The co-processed additive may be in the form of a physically bound composite whereby the lubricant is associated with the surface of the compression aid particles.

17 Claims, No Drawings

PHARMACEUTICAL COMPOSITION

This invention relates to a pharmaceutical composition. In particular, it relates to a co-processed additive for a solid-dose pharmaceutical composition and to solid-dose pharmaceutical compositions containing same.

In the pharmaceutical industry, the tabletting and encapsulation process involves the blending of excipients with the active ingredient to produce the tablets or capsules. Pharmaceutical compression aids are typically used in the formation of tablets and capsules. Once the materials are blended with the active ingredient, the last step before going to a tablet press is a short blending step with a lubricant, so that when the powder is compressed into tablets, the lubricant will lubricate the tablet press so that the tablets can be released. Without the lubricant, the tablets will stick to the dies of the press and break off or coat the dies. The lubricant most commonly used in the pharmaceutical industry is magnesium stearate. However, there are problems associated with the use of magnesium stearate such as overblending, which causes it to form sheets in the powder and results in poor lubrication. It also negatively affects the tablets resulting in weaker tablets and slower tablet dissolution.

It is an object of the invention to avoid or minimise the disadvantages of the prior art.

It has now unexpectedly been found that when a pharmaceutical compression aid is co-processed with a pharmaceutical lubricant, the resulting product is self-lubricating and when incorporated into solid-dose pharmaceutical compositions provides excellent lubrication and avoids the problems associated with the use of magnesium stearate alone as lubricant.

According to the invention there is provided a co-processed additive for a solid-dose pharmaceutical composition, the additive comprising from about 50% to 99.5% by weight of at least one pharmaceutical compression aid and from about 0.5% to 50% by weight of at least one pharmaceutical lubricant, the melting point of said compression aid(s) being higher than the melting point of said lubricant(s).

As used herein, the term "pharmaceutical compression aid" or "compression aid" is intended to mean a substance which is suitable for use in a solid-dose pharmaceutical composition and which helps achieve the desired compression characteristics of a powder material used for pharmaceutical tabletting or encapsulation.

As used herein, the term "pharmaceutical lubricant" or "lubricant" is intended to mean a substance which is suitable for use in a solid-dose pharmaceutical composition and which reduces friction between moving parts during compression or compaction of the components of said pharmaceutical composition.

As used herein, the term "co processed additive" or "co processed product" is intended to mean a product comprising at least one pharmaceutical compression aid and at least one pharmaceutical lubricant which are processed together, and preferably form a physically bound composite of compression aid and lubricant, before incorporation into a solid-dose pharmaceutical composition.

In one embodiment, the co-processed additive consists essentially of from about 50% to 99.5% by weight of a pharmaceutical compression aid and from about 0.5% to 50% by weight of a pharmaceutical lubricant, the melting point of the compression aid being higher than the melting point of the lubricant.

The co-processed additive may conveniently comprise or consist essentially of any of the following: from about 75% to about 99.5% by weight of the compression aid and from about 0.5% to about 25% by weight of the lubricant; or from about 80% to about 99% by weight of the compression aid and from about 1% to about 20% by weight of the lubricant; or from about 85% to about 98% by weight of the compression aid and from about 2% to about 15% by weight of the lubricant; or from about 90% to about 98% by weight of the compression aid and from about 2% to about 10% by weight of the lubricant.

In the co-processed additive of the invention, the melting point of the or each compression aid is preferably at least 10° C. higher, or at least 20° C. higher, or at least 30° C. higher, or at least 40° C. higher, or at least 50° C. higher, than the melting point of the or each lubricant.

Suitable compression aids for use in the co-processed additive of the invention include one or more of lactose, microcrystalline cellulose, modified starch, mannitol, dextrose, cellulose, magnesium carbonate, dibasic calcium phosphate dihydrate, calcium sulphite dihydrate and tricalcium phosphate. Preferred are lactose, microcrystalline cellulose and modified starch. The lactose may be anhydrous lactose or lactose monohydrate. The lactose monohydrate may be spray dried.

Suitable lubricants for use in the co-processed additive of the invention include one or more of sodium stearoyl lactate, sodium oleate, stearic acid, magnesium stearate, calcium stearate and fatty acid mono-and di-glycerides (hereinafter referred to as "monoglycerides") comprising at least 50% monoglycerides. The fatty acid monoglycerides suitable for use in the invention may be based on saturated, unsaturated or moderately saturated fatty acids. Fatty acid monoglycerides contain different levels of di- and even tri-glycerides depending on their origin. The fatty acid monoglycerides used in the co-processed additive of the invention comprise at least 50% monoglycerides, preferably at least 80% monoglycerides, and more preferably at least 90% monoglycerides. Preferred are the distilled monoglycerides commercially available under the trade name Myverol. Particularly preferred is Myverol 18-04 which is a saturated, purified monoglyceride derived from soybean oil and having a melting point of 66° C. (151° F.).

The co-processed additive of the invention may be in particulate, microparticulate, granular or powder form. Particles preferably have an average particle diameter less that about 800 μm The compression aid and lubricant used herein are preferably extrudable.

The co-processed additive of the invention contains from about 50% to 99.5% by weight of compression aid and from about 0.5% to 50% by weight of lubricant. The actual amounts used will depend on the nature of the compression aid and lubricant. For example, when the lubricant is Myverol 18-04, it is suitably present in an amount of about 4% by weight while the compression aid is present in an amount of about 96% by weight of the co-processed additive.

The co-processed additive is preferably in the form of a physically bound composite of the compression aid and lubricant. The lubricant is preferably associated with the outer surface of the compression aid particles.

The invention also provides a process for preparing the co-processed additive of the invention comprising:

(1) combining the compression aid and lubricant;
(2) subjecting the resulting combination to a temperature that is the same as, or higher than, the melting point of the lubricant, but is lower than the melting point of the compression aid, so that the lubricant when melted will be dispersed on the outer surface of the compression aid particles; and (3) reducing the temperature of the product of step (2) to a temperature below the melting point of the lubricant so as to form a physically bound composite of the compression aid and lubricant.

In step (1) above, the compression aid and lubricant may be blended together until a homogenous blend is obtained, conveniently for approximately 10 to 20 minutes.

In one embodiment, step (2) above may be carried out by extruding the combined compression aid and lubricant, the temperature during extrusion being such that the lubricant will melt but the compression aid, having a higher melting point, will not.

Preferably, the temperature in step (2) is at least 2° C. higher than the melting point of the lubricant and at least 8° C. lower than the melting point of the compression aid. More preferably, the temperature in step (2) is at least 10° C. or at least 20° C. higher than the melting point of the lubricant and at least 10° C. lower than the melting point of the compression aid.

When the lubricant melts, it is dispersed on the outer surface of the compression aid particles. If extrusion is used, when the product is released from the extruder, the lubricant solidifies on the surface of the compression aid particles as it is cooled, so that the surface of the compression aid particles is at least partially coated by the lubricant.

Preferably, at least 50%, more preferably at least 75%, of the surface of the compression aid particles is coated by the lubricant.

Typically, the extruder which may be used in the process of the invention has a plurality of temperature zones. In such an extruder, all of the zones apart from the final zone are preferably set at the desired temperature between the melting points of the lubricant and compression aid and the final zone is preferably left unheated so that the product exiting the extruder is at a temperature that is lower than the temperature of the extruder, thereby accelerating the solidification of the lubricant on the surface of the compression aid particles so as to form a physically bound composite of the compression aid and lubricant, the lubricant being associated with the outer surface of the compression aid particles.

The composite particles may be collected at an air temperature between about 15° C. and 25° C. (59° F.-77° F.). If necessary, particles having an average particle diameter greater than 800 μm may be removed from the collected particles, for example by sifting.

The invention also provides a solid-dose pharmaceutical composition comprising the co-processed additive according to the invention, and a therapeutically effective amount of a pharmacologically active ingredient.

The invention further provides the use of the co-processed additive of the invention in the preparation of a solid-dose pharmaceutical composition.

The pharmaceutical composition of the invention may be in a form suitable for oral administration, such as a tablet, capsule or pellet. The co-processed additive of the invention may be present in the pharmaceutical composition in an amount as low as about 30% by weight of the composition, typically from about 30% to about 99% or preferably from about 50% to about 99% by weight of the pharmaceutical composition.

Preferably, the pharmaceutical composition of the invention does not comprise magnesium stearate other than as a component of the co-processed additive of the invention.

The pharmaceutical composition according to the invention may be prepared by a process comprising the following steps:

(1) combining the co-processed additive of the invention with a therapeutically effective amount of a pharmacologically active ingredient;
(2) blending the resulting combination until a homogenous blend is obtained; and
(3) feeding the blend formed in step (2) to an apparatus suitable for formation of the pharmaceutical composition.

In step (1) of the process, optional conventional additives may be combined with the co-processed additive and active ingredient. The optional conventional additives may include one or more of disintegrants, sweetening agents, flavouring agents and the like.

Active agents which may be present in the pharmaceutical compositions of the invention include analgesics, antipyretics, antibiotics, antihistamines, gastrointestinal, cardiovascular and respiratory drugs, vitamins, dietary supplements and the like.

The apparatus in step (3) may be a tablet press.

The advantages of using the co-processed additive of the invention in the manufacture of solid-dose pharmaceutical compositions include the following:

No other lubricant, such as magnesium stearate, is required.
It avoids overblending of magnesium stearate which causes tablet uniformity variability and poor lubrication in conventional tablets leading to capping and sticking of tablets to the dies of the tablet press.
There is no formation of product "tails" where the end of the product is rejected due to the length of mixing with magnesium stearate.
The tablets, capsules or pellets containing the co-processed additive have faster dissolution due to the absence of water-insoluble free magnesium stearate.
Tablets are harder (stronger) than those formed with magnesium stearate alone as lubricant.
The formation of pharmaceutical compositions is simplified. Since free magnesium stearate is not present as lubricant, a second blending step (to incorporate the magnesium stearate) just prior to tabletting, encapsulation or pelleting is not required.
There is no yellowing in tablets containing lactose due to the absence of free magnesium stearate.

The invention will be illustrated in the following non-limiting Examples.

EXAMPLES

Example 1

A co-processed additive according to the invention was prepared with the following ingredients:

| Compression Aid: | Anhydrous Lactose | 181.14 kg (399.36 lb); | mp = 232° C. (450° F.) |
|---|---|---|---|
| Lubricant: | Distilled Monoglyceride (Myverol 18-04) | 7.56 kg (16.64 lb); | mp = 66° C. (151° F.) |

The compression aid (anhydrous lactose) was added to a 566.34 l (20 cubic foot) Littleford ribbon blender. The blender was turned on and the lubricant (distilled monoglyceride) was added to the blender. The compression aid and lubricant were blended for 20 minutes until a homogenous blend was formed. An APV 80 mm twin screw extruder with four temperature zones was used. The first three zones of the extruder were heated to approximately 127° C. (260° F.). The extruder was turned on and the blender valve was opened to begin product flow. The fourth zone of the extruder was unheated so that the temperature of the product leaving the extruder was between 49° C. and 71° C. (120° F.-160° F.). The product was collected from the extruder on a conveying belt at a temperature between 20° C. and 25° C. (68° F.-77° F.) and conveyed until the product had reached a temperature below 27° C. (80° F.). Particles having an average particle diameter greater than 800 μm were removed using a Sweco sifter with a 20 mesh screen. The resulting powder was then ready for packaging.

Example 2

The procedure of Example 1 was repeated except that the compression aid, anhydrous lactose, was replaced by spray dried lactose having a melting point of 202° C. (396° F.). The quantities of the compression aid and lubricant were the same as those used in Example 1.

Example 3

The procedure of Example 1 was repeated except that the compression aid, anhydrous lactose, was replaced by microcrystalline cellulose having a melting point of 243° C. (469° F.). The quantities of the compression aid and lubricant were the same as those used in Example 1.

Example 4

The procedure of Example 1 was repeated except that the lubricant, distilled monoglyceride, was replaced by magnesium stearate having a melting point of 88° C. (190° F.). The quantities of the compression aid and lubricant were the same as those used in Example 1.

Example 5

Tablets were produced from the co-processed product prepared in Example 1 containing 96% by weight anhydrous lactose and 4% by weight distilled monoglyceride, by pouring 100 g of the powder into the hopper of a Globe Pharma 10 station instrumented rotary tablet press. No blending was required. The press was turned on and run at 20 rpm, using 5 of the stations with 9.525 mm (⅜ inch) round tablet tooling. The compression force and ejection force were measured using the tablet press software. The tablet hardness was measured using a Cropharm tablet hardess tester. The tablets were then tested for distintegration using a distintegration apparatus as listed in the USP/NF (US Pharmacopoeia/National Formulary). The results are shown in Table 1. The tablets and tooling were also observed for capping and sticking, which are characteristics of insufficient or uneven lubrication.

TABLE 1

Tablet Data

| Compression Force (kg) | Compression Force (lbs) | Ejection Force (kg) | Ejection Force (lbs) | Hardness (N) | Disintegration (sec) |
|---|---|---|---|---|---|
| 301.96 | 665.7 | 3.99 | 8.8 | 16.5 | 586.3 |
| 385.96 | 850.9 | 4.85 | 10.7 | 23.4 | 716.0 |
| 460.40 | 1015.0 | 5.85 | 12.9 | 27.5 | 819.7 |
| 575.34 | 1268.4 | 7.35 | 16.2 | 35.8 | 1043.3 |
| 666.87 | 1470.2 | 8.53 | 18.8 | 39.6 | 1160.0 |

Observations: Throughout the run of 100 grams, the tablets produced were very smooth and slightly shiny. There were no tablet imperfections and no residue on the tablet press tooling.

Example 6

Tablets were produced according to the procedure of Example 5 except that 100 g of the co-processed powder prepared in Example 2 containing 96% by weight spray dried lactose and 4% by weight distilled monoglyceride were used. As in Example 5, no blending was required. The results obtained for the resulting tablets are shown in Table 2.

TABLE 2

Tablet Data

| Compression Force (kg) | Compression Force (lbs) | Ejection Force (kg) | Ejection Force (lbs) | Hardness (N) | Disintegration (sec) |
|---|---|---|---|---|---|
| 312.48 | 688.9 | 4.17 | 9.2 | 35.7 | 128.7 |
| 377.07 | 831.3 | 4.99 | 11.0 | 52.0 | 269.3 |
| 457.86 | 1009.4 | 6.12 | 13.5 | 70.4 | 404.0 |
| 535.69 | 1181.0 | 8.16 | 18.0 | 88.1 | 632.3 |

Observations: Throughout the run of 100 grams, tablets were very smooth and slightly shiny. There were no tablet imperfections and no residue on the tablet press tooling.

Example 7

Tablets were produced according to the procedure of Example 5 except that 100 g of the co-processed powder prepared in Example 3 containing 96% by weight microcrystalline cellulose and 4% by weight distilled monoglyceride were used. As in Example 5, no blending was required. The results obtained for the resulting tablets are shown in Table 3.

TABLE 3

Tablet Data

| Compression Force (kg) | Compression Force (lbs) | Ejection Force (kg) | Ejection Force (lbs) | Hardness (N) | Disintegration (sec) |
|---|---|---|---|---|---|
| 251.52 | 554.5 | 3.13 | 6.9 | 22.5 | 334.0 |
| 391.22 | 862.5 | 5.17 | 11.4 | 35.2 | 338.0 |
| 507.89 | 1119.7 | 5.99 | 13.2 | 49.8 | 409.0 |
| 586.49 | 1293.0 | 7.71 | 17.0 | 63.1 | 411.0 |

Observations: Throughout the run of 100 grams, tablets were very smooth and slightly shiny. There were no tablet imperfections and no residue on the tablet press tooling.

Example 8

Tablets were produced according to the procedure of Example 5 except that 100 g of the co-processed powder prepared in Example 4 containing 96% by weight anhydrous lactose and 4% by weight magnesium stearate were used. As in Example 5, no blending was required. The results obtained for the resulting tablets are shown in Table 4.

TABLE 4

| Compression Force (kg) | Compression Force (lbs) | Ejection Force (kg) | Ejection Force (lbs) | Hardness (N) | Disintegration (sec) |
|---|---|---|---|---|---|
| 283.95 | 626.0 | 4.22 | 9.3 | 28.3 | 723.6 |
| 446.38 | 984.1 | 7.39 | 16.3 | 42.7 | 795.0 |
| 628.23 | 1385.0 | 11.52 | 25.4 | 61.2 | 827.0 |

Observations: Throughout the run of 100 grams, tablets were very smooth and slightly shiny. There were no tablet imperfections and no residue on the tablet press tooling.

Example 9 (Comparative Example)

Tablets were produced according to the procedure of Example 5 except that the co-processed product was replaced by 99 g of anhydrous lactose and 1 g of magnesium stearate. These ingredients were blended together in a 5.66 l (0.2 cubic foot) laboratory ribbon blender for three minutes at 100 rpm before tabletting. The results obtained for the resulting tablets are shown in Table 5.

TABLE 5

| Compression Force (kg) | Compression Force (lbs) | Ejection Force (kg) | Ejection Force (lbs) | Hardness (N) | Disintegration (sec) |
|---|---|---|---|---|---|
| 304.18 | 670.6 | 3.22 | 7.1 | 21.0 | 657.7 |
| 370.63 | 817.1 | 3.99 | 8.8 | 23.2 | 636.7 |
| 454.59 | 1002.2 | 5.26 | 11.6 | 28.7 | 687.0 |
| 558.37 | 1231.0 | 6.94 | 15.3 | 37.9 | 689.7 |
| 640.29 | 1411.6 | 8.21 | 18.1 | 46.2 | 711.3 |

Observations: In the start of the run, the tablets were smooth and slightly shiny. Near the end of the run, the tablets were capping and sticking. It is assumed that this was due to the longer blending in the feed frame. There was also residue on the tablet press tooling. The blender was also coated with magnesium stearate after blending, which was hard to clean.

Example 10 (Comparative Example)

It was attempted to produce tablets according to the procedure of Example 5 except that the co-processed product was replaced by 100 g of anhydrous lactose powder in the absence of lubricant. No blending was required. No tablet data were obtained for the reasons given under observations below.

Observations: Within 2 rotations of the tablet press, the tablets were sticking to all of the tooling. The tablets were breaking off when they hit the tablet release plow and no intact tablets were released.

Conclusions

The tablet data obtained using the co-processed additives of the invention were at least as good as those obtained using magnesium stearate alone as the lubricant in relation to compression and ejection force and were significantly improved as regards hardness and disintegration while avoiding the problems associated with the use of magnesium stearate alone as lubricant.

The invention is not limited to the embodiments described herein but may be amended or modified without departing from the scope of the invention.

The invention claimed is:

1. A co-processed additive for a solid-dose pharmaceutical composition, the additive comprising from about 50% to 99.5% by weight of at least one pharmaceutical compression aid and from about 0.5% to 50% by weight of at least one pharmaceutical lubricant, the melting point of said compression aid(s) being higher than the melting point of said lubricant(s); wherein the additive is in the form of a physically bound composite of the compression aid and lubricant, the lubricant being associated with the outer surface of the compression aid such that no free lubricant is required prior to tableting, encapsulation or pelleting when the co-processed additive is incorporated in the solid-dose pharmaceutical composition, and wherein the lubricant is not magnesium stearate.

2. A co-processed additive for a solid-dose pharmaceutical composition, the additive consisting essentially of from about 50% to 99.5% by weight of at least one pharmaceutical compression aid and from about 0.5 to 50% by weight of at least one pharmaceutical lubricant, the melting point of said compression aid(s) being higher than the melting point of said lubricant(s); wherein the additive is in the form of a physically bound composite of the compression aid and lubricant, the lubricant being associated with the outer surface of the compression aid such that no free lubricant, is required prior to tableting, encapsulation or pelleting when the co-processed additive is incorporated in the solid-dose pharmaceutical composition, and wherein the lubricant is not magnesium stearate.

3. A co-processed additive according to claim 1 or 2, wherein the co-processed additive comprises from about 75% to about 99.5% by weight of the compression aid and from about 0.5% to about 25% by weight of the lubricant.

4. A co-processed additive according to claim 1 or 2, wherein the melting point of the or each compression aids is at least 10° C. higher than the melting point of the or each lubricant.

5. A co-processed additive according to claim 1 or 2, wherein the compression aid is selected from one or more of lactose, microcrystalline cellulose, modified starch, marmitol, dextrose, cellulose, magnesium carbonate, dibasic calcium phosphate dihydrate, calcium sulphite dihydrate and tricalcium phosphate.

6. A co-processed additive according to claim 5, wherein the compression aid is selected from one or more of lactose, microcrystalline cellulose and modified starch.

7. A co-processed additive according to any claim 1 or 2, wherein the lubricant is selected from one or more of sodium stearoyl lactate, sodium oleate, stearic acid, calcium stearate and fatty acid mono-and di-glycerides (hereinafter referred to as "monoglycerides") comprising at least 50% monoglycerides.

8. A co-processed additive according to claim 7, wherein the lubricant is selected, from one or more of fatty acid monoglycerides comprising at least 80% monoglycerides, and magnesium stearate.

9. A process for preparing a co-processed additive for a solid-dose pharmaceutical composition, the additive comprising from about 50% to 99.5% by weight of at least one pharmaceutical compression aid and from about 0.5% to 50% by weight of at least one pharmaceutical lubricant, the melting point of said compression aid(s) being higher than the melting point of said lubricant(s), wherein the additive is in the form of a physically bound composite of the compression aid and lubricant, the lubricant being associated with the outer surface of the compression aid such that no free lubricant is required prior to tableting, encapsulation or pelleting when the co-processed additive is incorporated in the solid-dose pharmaceutical composition, and wherein the lubricant is not magnesium stearate, the process comprising:

(1) combining the compression aid and lubricant;
(2) subjecting the resulting combination to a temperature that is the same as, or higher than, the melting point of the lubricant, but is lower than the melting point of the compression aid, so that the lubricant when melted will be dispersed on the outer surface of the compression aid particles; and
(3) reducing the temperature of the product of step (2) to a temperature below the melting point of the lubricant so as to form a physically bound composite of the compression aid and lubricant, the lubricant being associated with the outer surface of the compression aid.

10. A process according to claim 9, wherein step (2) is carried out by extruding the combined compression aid and lubricant at a temperature that is the same as, or higher than, the melting point of the lubricant, but is lower than the melting point of the compression aid.

11. A solid-dose pharmaceutical composition comprising a co-processed additive, and a therapeutically effective amount of a pharmacologically active ingredient, said co-processed additive comprising from about 50% to 99.5% by weight of at least one pharmaceutical compression aid and from about 0.5% to 50% by weight of at least one pharmaceutical lubricant, the melting point of said compression aid(s) being higher than the melting point of said lubricant(s); wherein the additive is in the form of a physically bound composite of the compression aid and lubricant, the lubricant being associated with the outer surface of the compression aid such that no free lubricant is required prior to tableting, encapsulation or pelleting when the co-processed additive is incorporated in the solid-dose pharmaceutical composition so that the solid-dose pharmaceutical composition contains no free lubricant, and wherein the lubricant is not magnesium stearate.

12. A solid-dose pharmaceutical composition according to claim 11, wherein the co-processed additive is present in the pharmaceutical composition in an amount of from about 30% to about 99% by weight of the composition.

13. A solid-dose pharmaceutical composition according to claim 11, which is in the form of a tablet, capsule or pellet for oral administration.

14. A method of using, comprising using the co-processed additive according to claim 1 or 2 in the preparation of a solid-dose pharmaceutical composition.

15. A process for preparing a solid-dose pharmaceutical composition according to claim 11, the process comprising the following steps:

(1) combining the co-processed additive defined in claim 11 with a therapeutically effective amount of a pharmacologically active ingredient;
(2) blending the resulting combination until a homogenous blend is obtained without the addition of free lubricant; and
(3) feeding the blend formed in step (2) to an apparatus suitable for formation of the solid-dose pharmaceutical composition.

16. A co-processed additive according to claim 3, wherein the co-processed additive consists essentially of from about 75% to about 99.5% by weight of the compression aid and from about 0.5% to about 25% by weight of the lubricant.

17. A co-processed additive according to claim 4, wherein the melting point of the or each compression aids is at least 50° C. higher than the melting point of the or each lubricant.

\* \* \* \* \*